(12) United States Patent
Robinson

(10) Patent No.: US 7,947,687 B2
(45) Date of Patent: May 24, 2011

(54) ANTINEOPLASTIC AND CURCUMIN DERIVATIVES AND METHODS OF PREPARATION AND USE

(76) Inventor: Byron C Robinson, Apopka, FL (US)

(*) Notice: Subject to any disclaimer, the term of this patent is extended or adjusted under 35 U.S.C. 154(b) by 876 days.

(21) Appl. No.: 11/926,261

(22) Filed: Oct. 29, 2007

(65) Prior Publication Data

US 2008/0200478 A1    Aug. 21, 2008

Related U.S. Application Data

(63) Continuation-in-part of application No. PCT/US2007/004289, filed on Feb. 16, 2007.

(60) Provisional application No. 60/774,061, filed on Feb. 16, 2006.

(51) Int. Cl.
C07D 403/14 (2006.01)
C07D 231/10 (2006.01)
A61K 31/415 (2006.01)

(52) U.S. Cl. ........ 514/256; 514/406; 514/691; 544/242; 548/373.1; 548/376.1; 568/378

(58) Field of Classification Search ................... 544/242; 548/373.1, 376.1; 568/378; 514/256, 406, 514/691
See application file for complete search history.

(56) References Cited

U.S. PATENT DOCUMENTS 6,673,843 B2    1/2004    Arbiser ...................... 514/679

OTHER PUBLICATIONS

Simone, Oncology: Introduction, Cecil Textbook of Medicine, vol. 1, pp. 1004-1010, 1996.*
Zhang et al., Curcumin inhibits cyclooxygenase-2 transcription in bile acid- and phorbol ester-treated human gastrointestinal epithelial cells, Carcinogenesis, vol. 20, No. 3, pp. 445-451, 1999.*
Tan et al., PubMed Abstract (Curcumin-induced cell cycle arrest and apoptosis in human acute promyelocytic leukemia HL-60 cells via Mmp changes and caspase-3 activation, Anticancer Res. Nov.-Dec. 2006; 26(6B): 4361-71), Nov. 2006.*

* cited by examiner

Primary Examiner — Deepak Rao
(74) Attorney, Agent, or Firm — Rissman Hendricks & Oliverio LLP

(57) ABSTRACT

This invention comprises antineoplastic curcumin derivatives and methods of preparation and use thereof. Particular reference is made to the following isomeric compounds

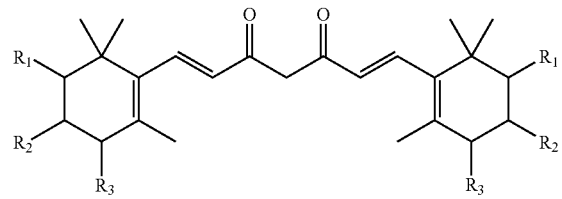

with R group variables

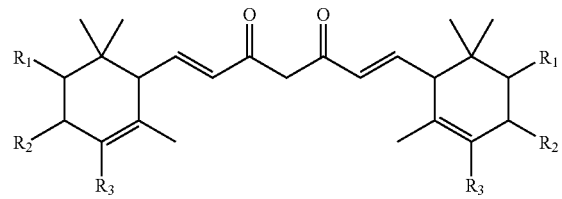

with R group variables

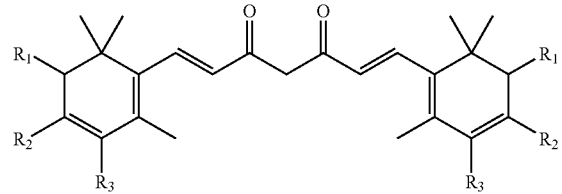

with R group variables wherein R1, R2, and R3 are selected from the group consisting of H, OH, OCH3, and COOH.

6 Claims, 3 Drawing Sheets

1,7,-bis-(2,6,6-trimethylcyclohex-1-en-1-yl)-1(E),6(E)-heptadiene-3,5-dione

Curcumin

ANTINEOPLASTIC AND CURCUMIN DERIVATIVES AND METHODS OF PREPARATION AND USE

CROSS REFERENCE TO RELATED APPLICATIONS

This patent application is a Continuation-in-Part of PCT Application No. US2007/004289 filed Feb. 16, 2007, which claims priority from U.S. Provisional Patent Application Ser. No. 60/774,061, filed on Feb. 16, 2006.

FIELD OF THE INVENTION

This invention comprises antineoplastic curcumin derivatives. Particular reference is made to the acylation product of the lithium enolate of β-ionone using the acid chloride, 2(E)-3-(2,6,6-trimethycyclohex-1-en-1-yl)propenoyl chloride derived from β-cyclocitral. Particular reference is made to the isomeric compound, 1-(2,6,6-trimethylcyclohex-2-en-1-yl)-7-(2,6,6-trimethylcyclohex-1-en-1-yl)-1,6-heptadiene-3,5-dione.

BACKGROUND

Kinetic studies on soybean LOX-3 and curcumin have shown a non-competitive mechanism of inhibition. Curcumin undergoes a photochemical reaction in the X-ray beam when trapped within LOX. LOX-3 becomes complexed with the X-ray induced oxidation and degradation product. Curcumin undergoes photolysis in the laser beam and it has been found that its cytoxicity is greatly enhanced by light. The photoproduct of curcumin binds as a peroxide in the central cavity of lipoxygenase in an Enz-Fe—O—O—R fashion facilitating the inhibition of LOX-3. Combinations of curcumin and retinoic acid have been to shown to have a particularly potent inhibitory effect on the proliferation of human promyelocyte leukemia HL-60 cells.

SUMMARY OF THE INVENTION

This invention comprises 1,7-bis-(2,6,6-trimethylcyclohex-1-en-1-yl)-1 (E)-heptadiene-3,5-dione, analogs and derivatives thereof as well as a method of therapeutically treating cancer by administering a therapeutic amount of 1,7-bis-(2,6,6-trimethylcyclohex-1-en-1-yl)-1(E)-heptadiene-3,5-dione to such subject This invention further comprises a curcumin derivative selected from the group consisting of

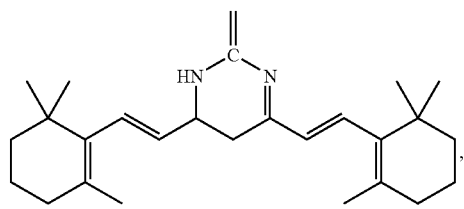
(13)

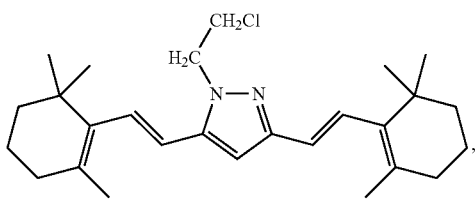
(14)

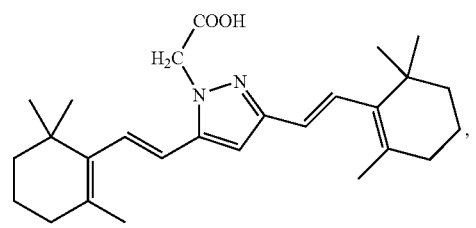
(15)

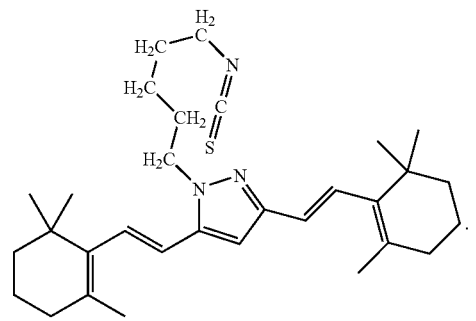
(16)

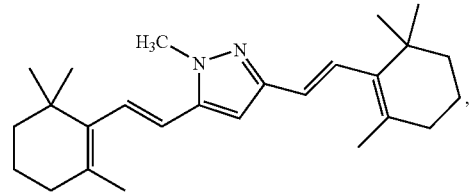
(17)

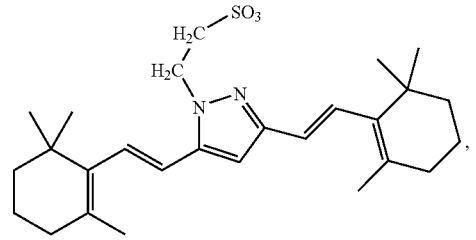
(18)

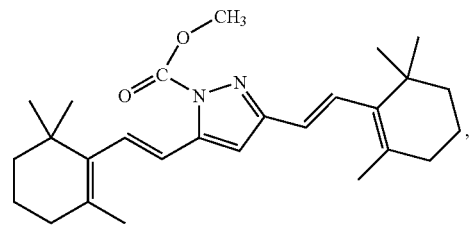
(19)

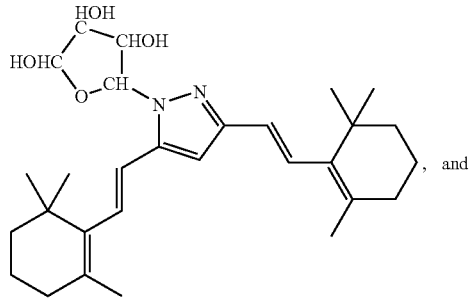

(20)

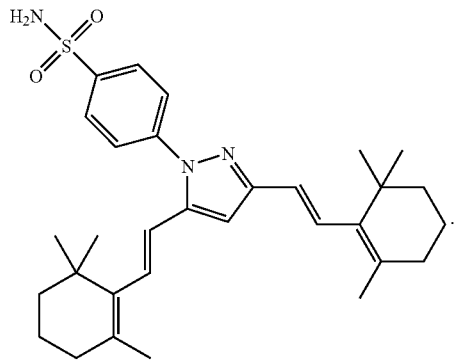

(21)

This further includes method of therapeutically treating cancer by administering a therapeutic amount of one or more such curcumin derivatives.

DETAILED DESCRIPTION OF THE INVENTION

Figure 1:
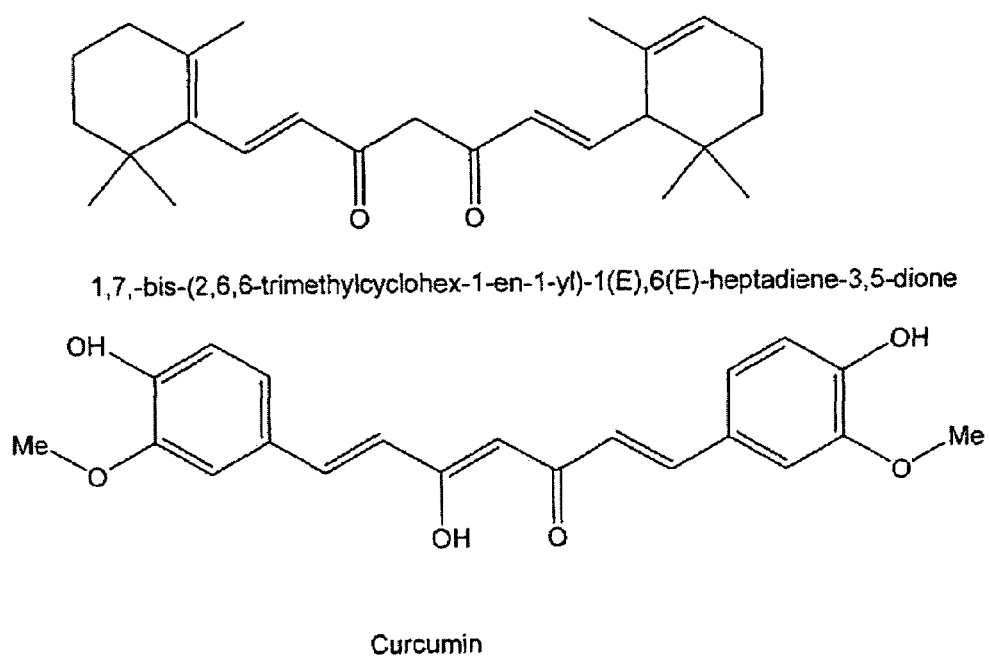
FIG. 1 shows structures for 1,7,-bis-(2,6,6-trimethylcyclohex-1-en-yl)-1(E),6(E)-heptadiene-3,5-dione and for curcumin.

Commercially available β-ionone (7, as shown in Scheme 1) and β-cyclocitral (3) were employed in the synthesis of 1,7-bis-(2,6,6-trimethylcyclohex-1-en-1-yl)-1(E),6(E)-heptadiene-3,5-dione (8) by the method outlined in Scheme 1. Triethyl phosphonoacetate (2) was prepared in 88% yield by heating a mixture of ethyl bromoacetate and triethyl phosphate. Treatment of (2) with potassium tert-butoxide in dimethyl formamide (DMF) generated the phosphonate anion which subsequently effected Wadsworth-Emmons-Horner olefination of β-cyclocitral (3).

The reaction proceeded in 65% yield with the expected E-selectivity. Without being bound by any particular theory, it is believed that during the course of the reaction, migration of the double bond in the cyclohexene ring occurred and a 64:36 mixture of compounds (4) and (4a) was obtained. See, Scheme 2.

Figure 2:
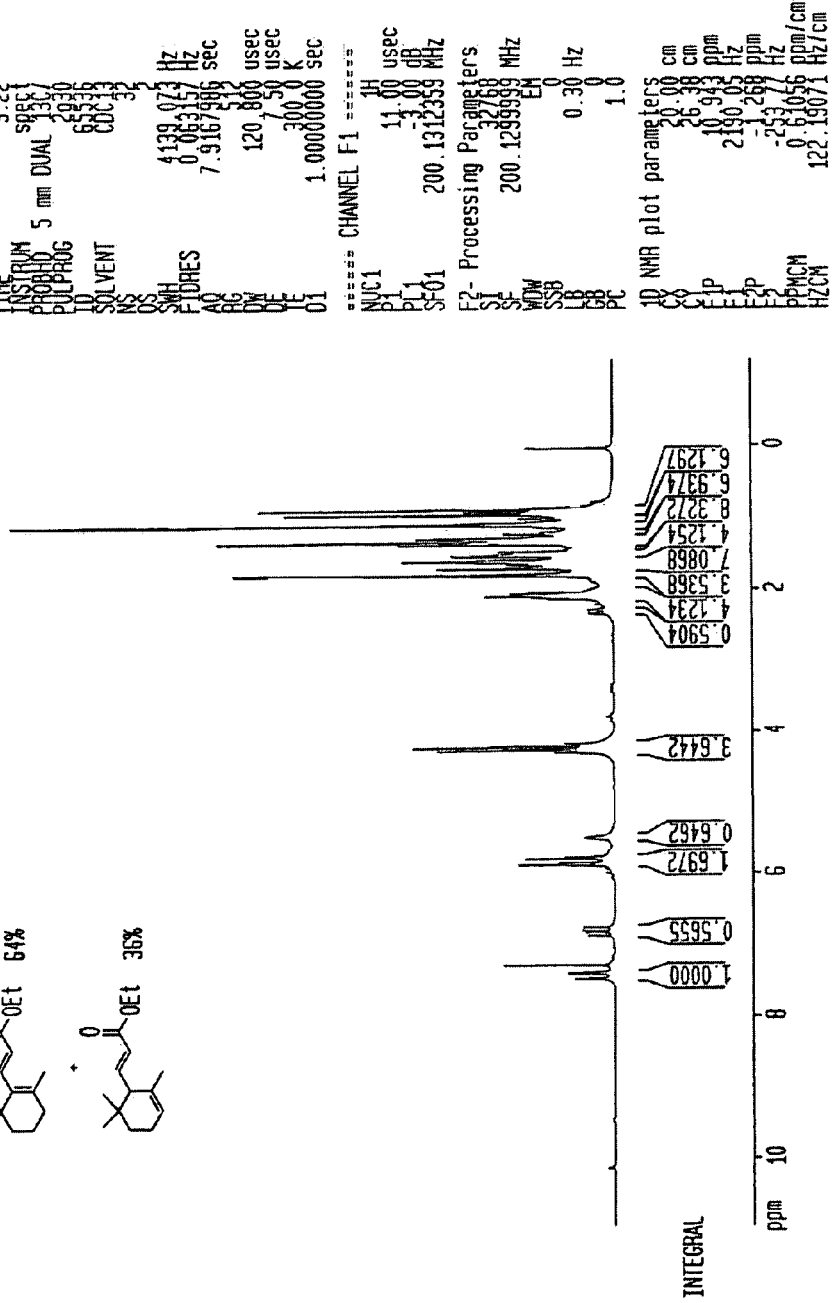
FIG. 2 shows an HNMR spectrum of the (4-4-a) mixture.

The $^1$HNMR spectrum (FIG. 2) of the (4-4-a) mixture features a pair of doublets at 7.41 (J=16.0 Hz) and 5.79 ppm (J=16.0 Hz). These are attributed to protons 2- and 3- of compound (4). Proton 3- of compound (4a) gives rise to a doublet of doublets at 6.82 ppm (J=16.0, 9.5 Hz) while the neighboring proton 2-gives rise to the doublet at 5.77 ppm (J=16.0 Hz). Proton 3'- of compound (4a) comes to resonance as a broad singlet at 5.48 ppm. A doublet at 2.30 ppm (J=9.5 Hz) is due to proton 1' of compound (4a).

Exposure of the mixture of olefinated products to basic conditions converted (4a) into the thermodynamically more stable compound (4). Base hydrolysis using "anhydrous potassium hydroxide" (KOBu$^t$, dry Et$_2$O, H$_2$O) followed by aqueous acid workup the acids (5) and (5a) (83% yield) in a ratio of 80:20 respectively. Scheme 3

Scheme 3

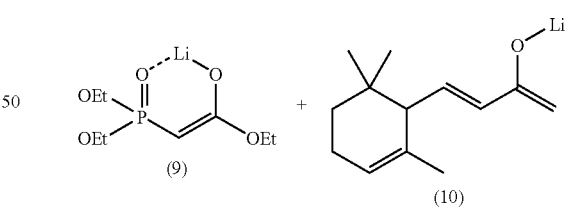

(5) 80%   (5a) 20%

In one embodiment, the sensitivity to base of β-cyclocitral (3) under the conditions of the Wadsworth-Emmons-Horner olefination as manifested by the double bond migration is addressed by using the Masamune-Roush conditions in which an organic base such as diisopropylethylamine or 1,8-Diazobicycloundec-[5.4.0]-ene (DBU) in the presence of a lithium salt effects the formation of the phosphonate anion. Again, without being bound by any particular theory, it is believed that the stability gained by formation of the chelate structure (9) allows for the use of the milder organic bases and complications associated with base sensitive carbonyl substrates are thereby avoided. Scheme 4.

Scheme 4

The mixture of acids (5) and (5a) was converted to the corresponding acid chlorides upon reaction with oxalyl chloride in THF in the presence of a catalytic amount of DMF. The acid chlorides were not isolated but were immediately made to react at −78° C. with the enolate (10) generated from β-ionone and lithium diisopropylamide (LDA). Workup and flash chromatography on silica eluting with 1% ethyl acetate in hexanes, followed by recrystallization from 95% ethanol furnished in 70% yield, the target compound, 1,7-bis-(2,6,6-trimethylcyclohex-1-en-1-yl)-1(E),6(E)-heptadiene-3,5-dione in a 86:14 mixture with the isomer (8a).

Scheme 5

Figure 3:
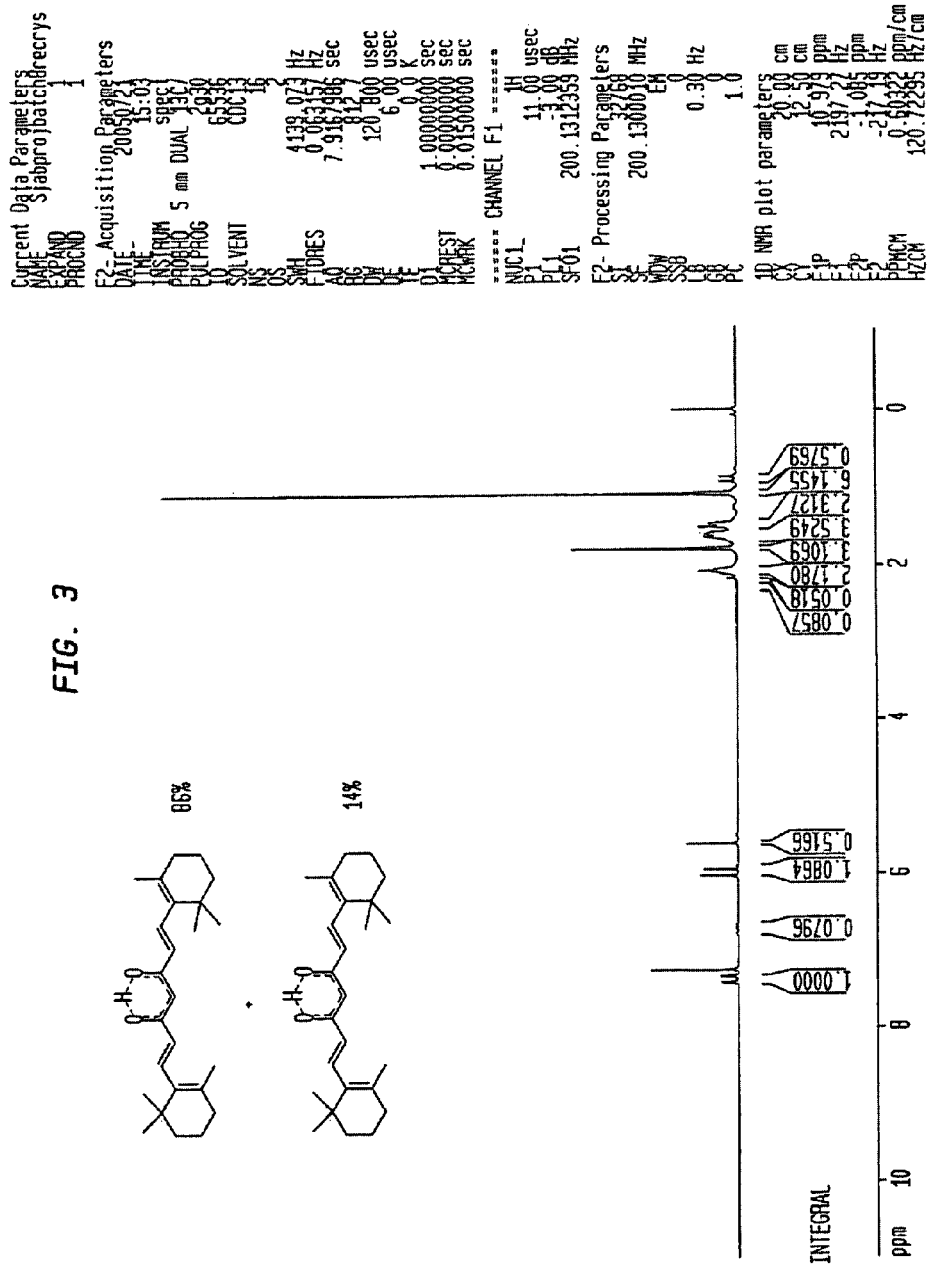
FIG. 3 show an HNMR spectrum of the (8-8a) mixture.

| Proton No. | Ppm (200 MHz, CDCl$_3$) | JHz | Ppm (200 MHz, CDCl$_3$) | JHz |
|---|---|---|---|---|
| $^1$H resonances for isomer (8a) are discernible in FIG. 3 An expanded spectrum allows for the assignment of chemical shifts for both (8) and (8a) in their enol forms (Table 1). | | | | |
| H-1 | 7.35 d | 16.0 | 6.68 dd | 16.0, 9.5 |
| H-2 | 5.98 d | 16.0 | 5.90 d | 16.0 |
| H-4 | 5.58 s | | 5.58 s | |
| H-6 | 5.98 d | | 5.98 d | 16.0 |
| H-7 | 7.35 d | | 7.35 d | 16.0 |
| H-1″ | | | 2.28 d | 9.5 |
| H-3′, 4″ | 2.09 m | | 2.09 m | |
| H-3 | | | 5.45 br s | |
| H-4′ | 1.62 m | | | |
| H-5′, 5″ | 1.48 m | | 1.48 m | |
| H-7′, 8′ | 1.09 s | | | |
| H-7″ | | | 0.93 s | |
| H-8″ | | | 0.85 s | |
| H-9′, 9″ | 1.80 s | | 1.80 s | |

TABLE 1

| Carbon No. | ppm (50 MHz, CDCl$_3$) |
|---|---|
| C-1 | 140.4 |
| C-2 | 136.59 |
| C-3, 5 | 183.56 |
| C-4 | 100.6 |
| C-1′ | 135.69 |
| C-2′ | 127.97 |
| C-3 | 33.65 |
| C-4′ | 18.94 |
| C-5′ | 39.82 |
| C-6′ | 34.19 |
| C-7′, 8′ | 28.85 |
| C-9′ | 21.81 |

This invention further comprises the following compound

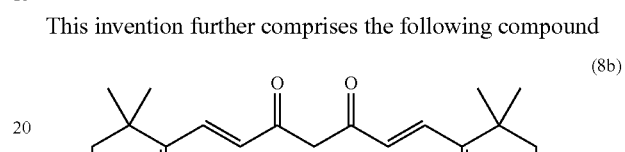

(8b)

It is understood that under physiological conditions this molecule exists as an equilibrium of its keto and enol tautomers. A synthesis for this compound is presented as Scheme 6 below.

Scheme 6

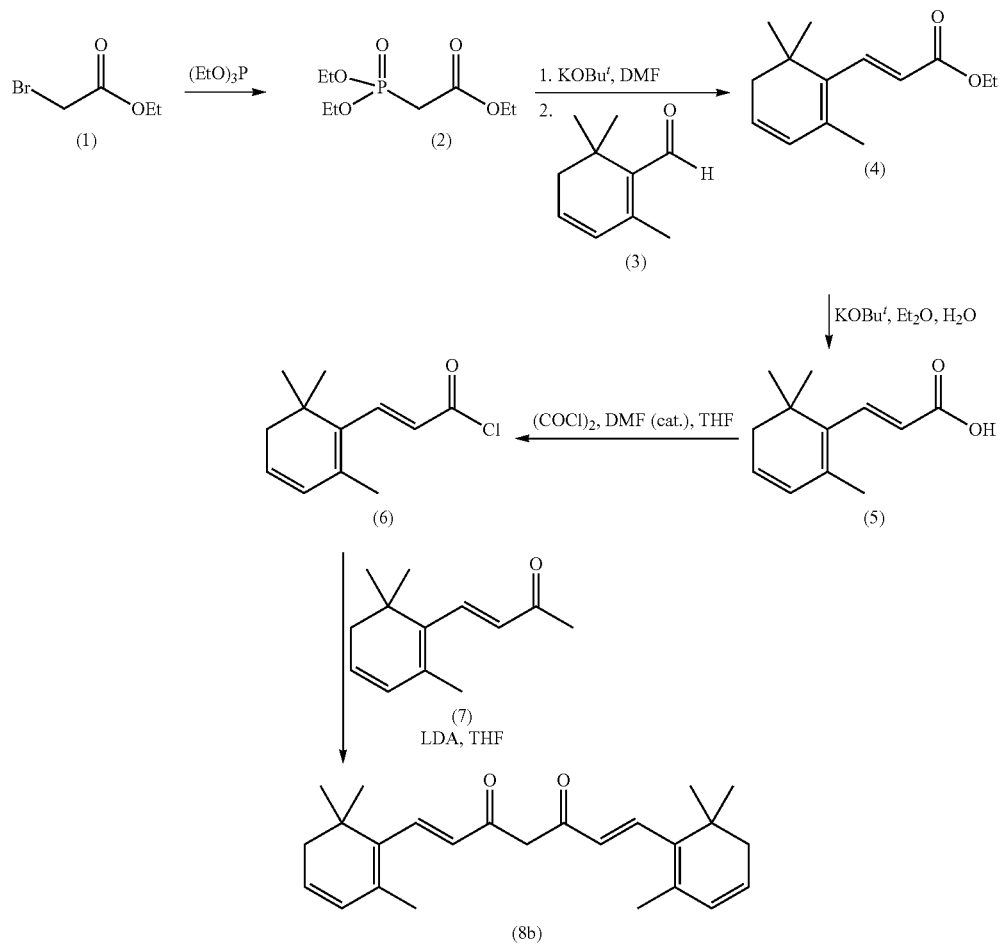

Experimental

NMR spectra were obtained on a Bruker Vector 2000-200 or a Bruker Vector 2000-500 spectrometer using tetramethylsilane as internal standard. IR spectra were run on a Bruker Vector 22 FTIR spectrometer. Melting points are uncorrected and were determined on a Thomas-Hoover melting point apparatus. Diethyl ether and tetrahydrofuran (THF) were distilled from sodium/benzophenone ketyl while dimethy formamide (DMF) was dried over 3 Å sieves then distilled at reduced pressure. Analytical thin layer chromatography (TLC) was performed on 250 μm silica and flash column chromatography on 230-400 mesh silica.

Triethyl Phosphonoacetate (2)

A mixture of ethyl bromoacetate (11.30 g, 7.5 mL, 67.6 mmol) and triethyl phosphate (11.63 g mmol, 12 mL, 1.05 equiv.) was heated with stirring in a sealed tube at 140° C. for 3 h. after which the crude mixture was distilled to give triethyl phosphonoacetate (13.39 g, 88%) as a colorless liquid. B.p. 93-94° C./0.8 mmHg (lit[2] 140° C./9 mmHg); $^1$H NMR (200 MHz, $CDCl_3$) δ 4.12 (m, 6H), 3.05 (s, 1H), 2.90 (s, 1H), 1.20-1.30 (m, 9H).

Ethyl 2(E)-3-(2,6,6-trimethylcyclohex-1-en-1-yl)propenoate (4) and Ethyl 2(E)-3-(2,6,6-trimethylcyclohex-2-en-1-yl)propenoate (4a)

Triethyl phosphonoacetate (4.97 g, 4.4 mL, 22.2 mmol) was added dropwise to a slurry of potassium tert-butoxide (2.53 g, 22.5 mmol) in DMF (15 mL) at 0° C. The mixture was brought to room temperature and stirred for 1 h under an atmosphere of nitrogen. B-Cyclocitral (3) (3.38 g, 3.52 mL, 22.2 mmol) was added over a period of 15 min. with the temperature maintained below 30° C. The yellow suspension was stirred at room temperature for 20 h at which point TLC indicated that the reaction was not complete. An additional portion of potassium tert-butoxide (1.27 g, 11.3 mmol, 0.5 equiv.) was added and the mixture stirred for a further 27 h. The reddish-brown reaction mixture was poured into 130 mL of water and was extracted with ether. After drying over sodium sulphate, the ethereal solution was evaporated under vacuum to give a pale yellow liquid (4.15 g). Flash chromatography on silica eluting with hexanes gave a mixture of esters (4) and (4a) as a pale yellow oil (3.16 g, 65%). Ethyl 2(E)-3-(2,6,6-trimethylcyclohex-1-en-1-yl)propenoate (4): 64% of mixture; $^1$H NMR (200 MHz, $CDCl_3$) δ 7.41 (d, J=16.0 Hz, 1H), 5.79 (d, J=16.0 Hz, 1H), 4.22 (m, 2H), 2.07 (m, 2H), 1.78 (s, 3H), 1.70-1.20 (m, 7H), 1.09 (s, 6H). Ethyl 2(E)-3-(2,6,6-trimethylcyclohex-2-en-1-yl)propenoate (4a): 36% of mixture; $^1$H NMR (200 MHz, $CDCl_3$) δ 6.82 (dd, J=16.0, 9.5 Hz, 1H), 5.77 (d, J=16.0 Hz, 1H), 5.77 (br s, 1H), 4.22 (m, 2H), 2.30 (d, J=9.5 Hz, 1H), 1.78 (s, 3H), 2.07 (m, 2H), 1.70-120 (m, 5H), 0.92 (s, 3H), 0.82 (s, 3H)

2(E)-3-(2,6,6-Trimethylcyclohex-1-en-1-yl)propenoic acid (5) and 2(E)-3-(2,6,6-trimethylcyclohex-2-en-1-yl)propenoic acid (5a)

Water (0.55 mL, 30.5 mmol) was added to a suspension of potassium tert-butoxide (12.79 g, 0.114 mol) in anhydrous diethyl ether (80 mL) whilst cooling in an ice bath. The mixture was stirred under an atmosphere of nitrogen for 5 min. then an ethereal solution of the 64:36 mixture of propenoates (4) and (4a) (3.14 g, 14.2 mmol) was added over a period of 5 min. The reaction mixture was stirred at 0-5° C. for 1 h then at room temperature for 30 h when TLC indicated that the reaction was complete. The reaction was quenched with cold water (5 mL) then was further diluted with water until two distinct layers were seen. The two phases were separated and whilst cooling in ice, the aqueous phase was acidified with 5% hydrochloric acid to pH 6. The white precipitate was extracted into diethyl ether. This process of acidification and extraction was repeated until the aqueous layer was pH 3 and no longer yellow but colorless. The combined ether extracts were dried over anhydrous sodium sulphate and evaporated under vacuum to give a mixture of the acids (5) and (5a) as a yellow-white waxy solid (2.47 g, 90%). IR (KBr disc) 3000-2500 br, 2929, 2865, 1685, 1630 $cm^{-1}$ 2(E)-3-(2,6,6-Trimethylcyclohex-1-en-1-yl)propenoic acid (5): 80% of mixture; $^1$HNMR (200 MHz, Acetone-$d_6$) δ 7.30 (d, J=16.0 Hz, 1H), 5.65 (d, J=16.0 Hz, 1H), 1.91 (m, 2H, 1.60 (s, 3H), 1.43 (m, 2H), 0.95 (s, 6H).

2(E)-3-(2,6,6-Trimethylcyclohex-2-en-1-yl)propenoic acid (5a): 20% of mixture; $^1$HNMR (200 MHz, Acetone-$d_6$) δ 6.61 (dd, J=16.0, 9.5 Hz, 1H), 5.70 (d, J=16.0 Hz, 1H), 5.33 (br s, 1H), 2.23 (d, J=9.5 Hz, 1H), 1.91 (m, 2H), 1.60 (s, 3H), 1.36 (m, 2H), 0.75 (s, 3H), 0.66 (s, 3H).

1,7-bis-(2,6,6-Trimethylcyclohex-1-en-1-yl)-1(E),6(E)-heptadiene-3,5-dione (8a) and 1-(2,6,6-trimethylcyclohex-2-en-1-yl)-7-(2,6,6-trimethylcyclohex-1-en-1-yl)-1(E),6(E)-heptadiene-3,5-dione (8a)

Acid chlorides were prepared by the addition of oxalyl chloride (0.8 mL, 91.6 mmol) and DMF (2 drops) to a solution in THF (15 mL) of the mixture of acids (5) and (5a) (1.55 g, 8.0 mmol). The solution was stirred at room temperature under an atmosphere of nitrogen for 3 h then was evacuated to remove solvent and excess oxalyl chloride. The dark brown residual liquid was set aside for later use.

Lithium diisopropylamide (LDA) was prepared by the dropwise addition of butyl lithium (10 mL of a 2.5M solution in hexanes, 25 mmol) to a solution of diisopropylamine (3.5 mL, 25 mmol) in THF (17 mL) at −78° C. under a nitrogen atmosphere. B-Ionone (7) (5.2 mL, 25 mmol) in THF (5 mL) was added dropwise to the freshly prepared solution of LDA and the mixture stirred at −78° C. for 5 min. A solution of the acid chlorides in THF (8 mL) was then added dropwise and the mixture stirred at −78° C. for 1 h. The cooling bath was brought up to 0° C. over a period of 45 min and the reaction mixture was stirred at this temperature for a further 1 h. after which it was poured into a mixture of crushed ice (18 g) and concentrated hydrochloric acid (4.8 mL). The organic layer was separated, diluted with diethyl ether, washed with saturated sodium bicarbonate solution followed by water and then dried over sodium sulphate. Evaporation under vacuum followed by flash chromatography furnished a mixture of compounds (8) and (8a) as a yellow solid (2.13 g, 70%). Recrystallization from 95% ethanol furnished yellow crystals. M.p. 104-106° C.; IR (KBr disc) 2929, 1685, 1630, 1373 $cm^{-1}$.

1,7-bis-(2,6,6-Trimethylcyclohex-1-en-1-yl)-1(E),6(E)-heptadiene-3,5-dione (8a)

86% of mixture; $^1$HNMR (200 MHz, $CDCl_3$) δ 7.35 (d, J=16.0 Hz, 2H), 5.98 (d, J=16.0 Hz, 2H), 5.58 (s, 1H), 2.09 (m, 4H), 1.80 (s, 6H), 1.62 (m, 4H), 1.48 (m, 4H), 1.09 (s, 12H); $^{13}$C NMR (50 MHz, $CDCl_3$) δ 183.56, 140.04, 136.59, 135.69, 127.97, 100.60, 39.82, 34.19, 33.65, 28.85, 21.81, 18.94.

1-(2,6,6-trimethylcyclohex-2-en-1-yl)-7-(2,6,6-trimethylcyclohex-1-en-1-yl)-1(E),6(E)-heptadiene-3,5-dione (8a): 14% of mixture; $^1$HNMR (200 MHz, $CDCl_3$) δ 7.35 (d, J=16.0 Hz, 1-H), 6.68 (dd, J=16.0, 9.5 Hz), 5.98 (d, J=16.0 Hz, 1H), 5.90 (d, J=16.0 Hz, 1H), 5.58 (s, 1H), 5.45 (br s, 1H), 2.28 (d, J=9.5 Hz, 1H), 2.09 (m, 4H, 1.80 (s, 6H), 1.48 (m, 4H), 0.93 (s, 6H), 0.85 (s, 6H)

The chemical structure of one exemplary antineoplastic curcumin derivatives is related to the compound curcumin and other β-diketones which have been shown to have anti-cancer or antineoplastic properties.

Studies have demonstrated the involvement of aberrant arachidonic acid metabolism in carcinogenesis. Membrane phospholipids, the major source of arachidonic acid are hydrolyzed by phospholipase $A_2$ ($PLA_2$); the released arachidonic acid is further metabolized by three different types of oxygenases: cyclooxygenase (COX), lipoxygenase (LOX) and cytochrome P450. Modulation of arachidonic acid metabolism by inhibiting these enzymes has been considered as an effective mechanism for chemoprevention. Inhibition of arachidonic acid metabolism by curcumin has been suggested to be a key mechanism for its anticarcinogenic action (1-3). Curcumin has been reported to inhibit COX-2 expression in gastrointestinal cancer cells and mouse skin (4-6). It has also been reported that curcumin affects the formation of COX- and LOX-dependent metabolites and decrease activities of $PLA_2$ and PLCγ (7,8). It has been suggested the curcumin affects arachidonic acid metabolism by blocking the phosphorylation of $cPLA_2$, decreasing the expression of COX-2 and inhibiting the catalytic activities of LOX (9).

In one embodiment, the new compounds are composed of two trimethyl hexame rings separated by a double-ketone. This is believed to lend itself to photoreaction that dramatically increases the anti-cancer effects of curcumin. The photoproduct of curcumin binds and inhibits LOX-3. The portion of the photoproduct of curcumin that sits in the binding pocket of LOX-3, would be identical to the photoproduct produced of the compound.

Without being bound by any particular theory, the trimethyl hexane ring in our new compound enters the cancer cell, opens with it, and destroys it without harming the surrounding, normal, cells. The toxicity level of our new chemical compound is extremely low, a key benefit for cancers patients who suffer from low immunity. The formulation of this chemical compound causes no known adverse reactions or side effects in patients.

Additional compounds of the present invention are also noted.

(13)

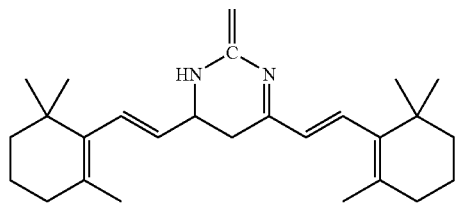

(14)

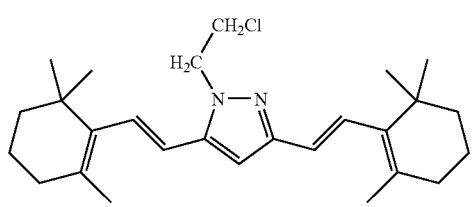

(15)

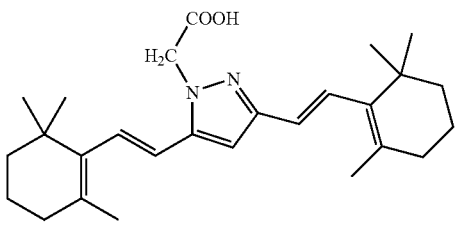

(16)

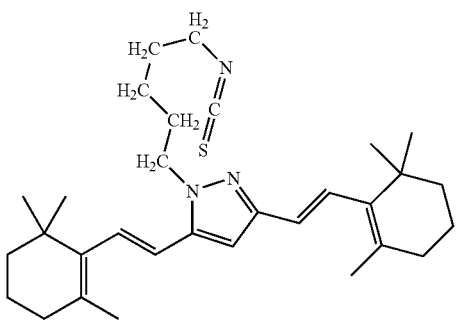

(17)

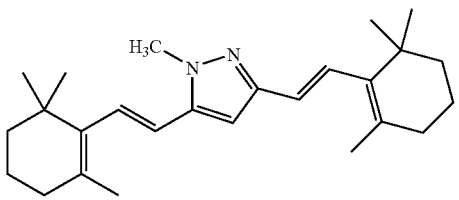

(18)

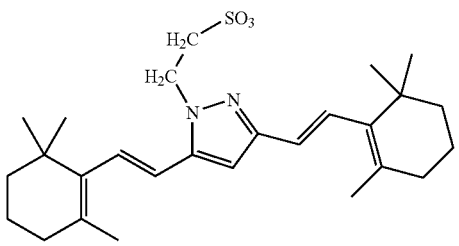

(19)

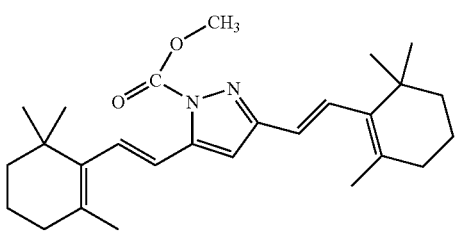

(20)

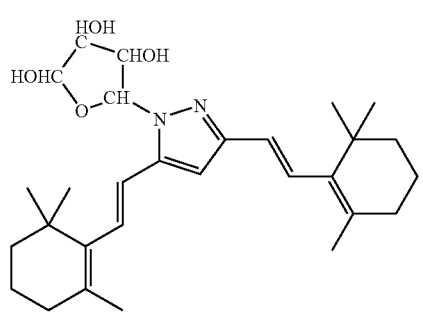

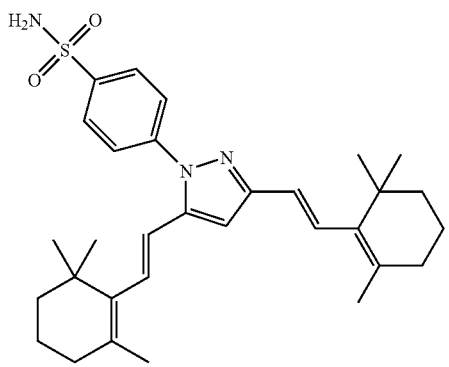

(21)

According to this invention, a therapeutically or pharmaceutically effective amount of antineoplastic curcumin derivatives are administered to subjects (with particular reference to mammals, and more particular reference to humans) to treat or prevent neoplastic disease with particular reference to cancer. In particular embodiments the antineoplastic curcumin derivatives of this invention therapeutically treat neuroblastoma, pancreatic, ovarian, prostate, endometrial, cervical and colorectal cancers as well as lymphoma and leukemia.

A therapeutically effective dose will depend upon the nature of the disease, the severity and course of the disease, previous therapy, the patient's health status, response to the antineoplastic curcumin derivative and the judgment of the treating medical caregiver. Typically, at least one antineoplastic curcumin derivative is administered as a sole active ingredient, or in combination with one or more other active ingredients. Typically co-administered drugs are N2-mercaptopropionylglycine, N-acetylcysteine, glutathione, dimethyl thiourea, desferrioxamine, mannitol, α-tocopherol, ascorbate, buthionine sulfoximine, allopurinol, 21-aminosteroids, calpain inhibitors, glutamate receptor antagonists, tissue plasminogen activator, streptokinase, urokinase, nonsteroidal anti-inflammatory agent, cortisone, and carotenoids. Antineoplastic curcumin derivatives are also be administered in conjunction with polypeptides having SOD and/or catalase activity.

The present invention includes a method of treating patients who have a neoplasticity associated disease with a prophylactically effective or therapeutically effective amount of an antineoplastic curcumin derivative. This method is useful to treat patients at various stages of their diseases or to prevent development of such diseases. In addition, the treatment can be administered to prevent or reduce the incidence of developing a neoplasm.

In some instances, a dosage of about 5 to 5000 mg will be administered to a patient either in single or multiple doses. In general, for treatment of neoplastic diseases, a therapeutically effective dose of antineoplastic curcumin derivative will be in the range of about 0.1 to 100 milligram (mg) per kilogram (kg) of body weight of recipient per day, and particularly in the range of about 1 to 20 mg per kg of body weight per day. The desired dosage is usefully presented in one, two, three, four or more subdoses administered at appropriate intervals throughout the day. These subdoses are administered as unit dosage forms, for example, containing about 5 to 10,000 mg, and particularly about 10 to 2000 mg of antineoplastic curcumin derivative per unit dosage form.

The composition used in these therapies can be in a variety of forms. These include, for example, solid, semi-solid and liquid dosage forms, such as tablets, pills, powders, liquid solutions or suspensions, liposome preparations, injectable and infusible solutions. The preferred form depends on the intended mode of administration and therapeutic application. Typically, a sterile solution of antineoplastic curcumin derivative in an aqueous solvent (e.g., saline) will be administered intravenously. The contemplated compositions also include pharmaceutically acceptable carriers and adjuvants which are known to those of skill in the art. See, e.g., *Remington: The Science and Practice of Pharmacy*, Ed. Randy Hendrickson, Lippincott, Williams & Wilkins, 21$^{st}$ Edition (2005). Generally, administration will be by oral or parenteral (including subcutaneous, intramuscular, intravenous, and intradermal) routes, or by topical application or infusion into a body cavity, or as a bathing solution for tissues during surgery.

It should, of course, be understood that the methods of this invention are usefully employed in combination with antioxidant agents that have SOD (superoxide dismutase) activity, catalase activity, glutathione peroxidase (GSH-Px)) activity, or are free radical scavengers or inhibitors of free radical formation. It is possible to administer the active ingredient of this invention as a single active pharmaceutical agent, and also as part of a pharmaceutical formulation. The pharmaceutically acceptable formulations of the present invention comprise at least one compound of this invention in a therapeutically or pharmaceutically effective dose together with, optionally, one or more pharmaceutically or therapeutically acceptable carriers and optionally other therapeutic ingredients. Carriers include inert, non-toxic solids (e.g., mannitol, talc) and buffered saline. Various considerations are described in, for example, *Goodman and Gilman's: The Pharmacological Bases of Therapeutics*, Eds. Laurence Brunton, John Lazo, Keith Parker 11 th Ed., Pergamon Press (2005); and Remington's supra, each of which is hereby incorporated herein by reference. Methods for administration are discussed therein, e.g., for oral, intravenous, intraperitoneal, or intramuscular administration, and others. Pharmaceutically acceptable carriers will include water, saline, buffers, and other compounds described in a number of sources including the *Merck Index*, Merck & Co., Rahway, N.J., incorporated herein by reference. As used herein, the term "pharmaceutically acceptable carrier" encompasses any of the standard pharmaceutical carriers such as sterile solutions, tablets, coated tablets, and capsules. Typically such carriers contain excipients such as starch, milk, sugar, certain types of clay, gelatin, stearic acids or salts thereof, magnesium or calcium sterate, talc, vegetable fats or oils, gums, glycols, or other known excipients. Such carriers may also include flavor and color additives or other ingredients. Compositions comprising such carriers are formulated by well known conventional methods.

Depending on the intended mode of administration and the intended use, the compositions may be in the form of solid, semi-solid, or liquid dosage forms, such, for example, as powders, granules, crystals, liquids, suspensions, liposomes, pastes, cremes, salves, etc., and may be in unit-dosage forms suitable for administration of relatively precise dosages. For semi-solid compositions, as would be appropriate for pastes and creams intended for topical administration, the antineoplastic curcumin derivatives are provided separately or may be compounded with conventional nontoxic carriers such as, for example, aloe vera gel, squalane, glycerol sterate, polyethylene glycol, cetyl alcohol, stearic acid, and propylene glycol, among others. Such compositions may contain about 0.005-100% active ingredient, more particularly about 0.5-25%. The concentration of antineoplastic curcumin derivatives in these formulations varies widely. Selection of a specific concentration may consider intended use, viscosities, etc., in accordance with the particular mode of administration selected. Typical compositions include lotions containing water and/or alcohols and emollients such as hydrocarbon oils and waxes, silicone oils, vegetable, animal or marine fats or oils, glyceride derivatives, fatty acids or fatty acid esters or alcohols or alcohol ethers, lecithin, lanolin and derivatives, polyhydric alcohols or esters, wax esters, sterols, phospholipids and the like, and generally also emulsifiers (nonionic, cationic or anionic), although some of the emollients inherently possess emulsifying properties. These same general ingredients are be formulated into a cream rather than a lotion, or into gels, or into solid sticks by utilization of different proportions of the ingredients and/or by inclusion of thickening agents such as gums or other forms of hydrophillic colloids. Such compositions are referred to herein as dermatologically acceptable carriers.

The pharmaceutical compositions will be administered by parenteral or oral administration for prophylactic and/or therapeutic treatment. The pharmaceutical compositions can be administered in a variety of unit dosage forms depending upon the method of administration. For example, unit dosage forms suitable for oral administration include powder, tablets, pills, capsules, trochees, and dragees.

The pharmaceutical compositions will often be administered intravenously. Thus, this invention provides compositions for intravenous administration which comprise a solution of the compound dissolved or suspended in an acceptable carrier, with specific reference to an aqueous carrier. A variety of aqueous carriers can be used, e.g., water, buffered water, 0.4% saline, and the like. Often, an antineoplastic curcumin derivative is dissolved in an organic solvent (e.g., dimethylsulfoxide) and either applied directly or diluted into an aqueous solvent. Typically, antineoplastic curcumin derivatives that are relatively lipophilic (e.g., C9, C12 and greater than C12) are dissolved in an organic solvent such as DMSO and, if desired, subsequently diluted into a more polar solvent, such as water. These compositions will sometimes be sterilized by conventional, well known sterilization techniques, or sterile filtered. The resulting aqueous solutions can be packaged for use as is, or lyophilized, the lyophilized preparation being combined with a sterile aqueous solution prior to administration. The compositions usefully contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, and the like.

For solid compositions, conventional nontoxic solid carriers can be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 0.001-95% of active ingredient, with particular reference to about 20%.

The compositions containing the compounds are usefully administered for prophylactic and/or therapeutic treatments. In therapeutic applications, compositions are administered to a patient already suffering from a disease, as described above, in an amount sufficient to cure or at least partially arrest the symptoms of the disease and its complications. An amount adequate to accomplish this is defined as "therapeutically effective amount or dose." Amounts effective for this use will depend on the severity of the disease and the weight and general state of the patient.

In prophylactic applications, compositions containing the compounds of the invention are administered to a patient susceptible to or otherwise at risk of a particular disease. Such an amount is defined to be a "prophylactically effective amount or dose." In this use, the precise amounts again depend on the patient's state of health and weight.

For solid compositions, conventional non-toxic solid excipients include, for example, pharmaceutical grades of mannitol, lactose, starch, magnesium stearate, talcum, celluloses, glucose, sucrose, magnesium carbonate, and the like may be used. The active compound as defined above may be formulated as suppositories using, for example, triglycerides, for example, any pharmaceutically acceptable Hard Fat NF bases (e.g., WITEPSOL®™, Condea Vista Company, Cranford, N.J.), as the carrier. Liquid pharmaceutically administerable compositions can, for example, be prepared by dissolving, dispersing, etc. an active compound as defined above and optional pharmaceutical adjuvants in a excipient, such as, for example, water, saline, aqueous dextrose, glycerol, ethanol, and the like, to thereby form a solution or suspension. If desired, the pharmaceutical composition to be administered may also contain minor amounts of inert auxiliary substances such as wetting or emulsifying agents, pH buffering agents and the like, for example, sodium acetate, sorbitan monolaurate, triethanolamine sodium acetate, triethanolamine oleate, etc. Actual methods of preparing such dosage forms are known, or will be apparent, to those skilled in this art; for example, see *Remington: The Science and Practice of Pharmacy*, Ed. Randy Hendrickson, Lippincott, Williams & Wilkins, $21^{st}$ Edition (2005). The composition or formulation to be administered will, in any event, contain an effective amount of the active compound(s).

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of inert auxiliary substances such as wetting or emulsifying agents, pH buffering agents and the like, such as for example, sodium acetate, sorbitan monolaurate, triethanolamine oleate, etc.

A more recently devised approach for parenteral administration employs the implantation of a slow-release or sustained-release system, such that a constant level of dosage is maintained. See, e.g., U.S. Pat. Nos. 5,629,008, 5,851,547, 6,183,461, and 3,710,795, which are incorporated herein by reference. Antineoplastic curcumin derivatives may be administered by transdermal patch (e.g., iontophoretic transfer) for local or systemic application.

Once detectable improvement of the patient's conditions has occurred, a maintenance dose is administered if necessary. Subsequently, the dosage or the frequency of administration, or both, is reduced, as a function of the symptoms, to a level at which the improved condition is retained. When the symptoms have been alleviated to the desired level, treatment can cease. Patients can, however, require intermittent treatment on a long-term basis upon any recurrence of the disease symptoms or as a prophylactic measure to prevent disease symptom recurrence. In particular embodiments extended release formulations are contemplated.

Antineoplastic curcumin derivatives are also be added to extravasated blood for transfusion to inhibit oxyradical damage to the blood cells and components during storage; similarly, antineoplastic curcumin derivatives reduce oxyradical damage to blood cells in vivo.

Antineoplastic curcumin derivatives are usefully added to rinse or storage solutions for organs and tissues, such as for organ transplantation or for surgical rinses. For example, excised organs are often placed in a preservation solution prior to transplant into a recipient. Inclusion of at least one antineoplastic curcumin derivatives in a preservation solution, usually at a concentration of about 0.01 mM to 10 mM, is useful for reducing damage due to ischemia during storage and reperfusion injury following reimplantation in the recipient.

Typically a antineoplastic curcumin derivatives is present in the rinse or storage solution at a concentration of about 10 microM to about 10 mM, and most usually is present at 1 mM. For example, but not to limit the invention, a suitable rinse solution comprises Ringer's solution (102 mM NaCl, 4 mM KCl, 3 mM $CaCl_2$, 28 mM sodium lactate, pH 7.0) or Ringer's solution with 0.1 mM adenosine, and the antineoplastic curcumin derivatives at a final concentration of 1 mM. The rinse solution can further comprise additional antioxidants (e.g., glutathione, allopurinol). Preservation or rinse solutions containing antineoplastic curcumin derivative is used to provide enhanced storage or irrigation of organs (e.g., kidney, liver, pancreas, lung, fetal neural tissue, heart, vascular grafts, bone, ligament, tendon, skin) which is believed to enhance the viability of the tissue and increase resistance to oxidative damage (e.g., as a consequence of ischemia/reperfusion).

Scheme 2

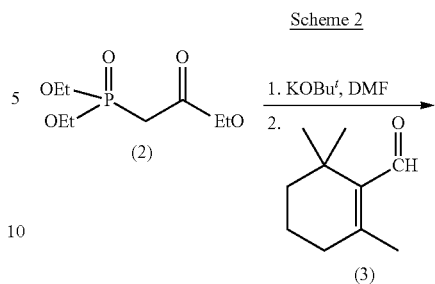

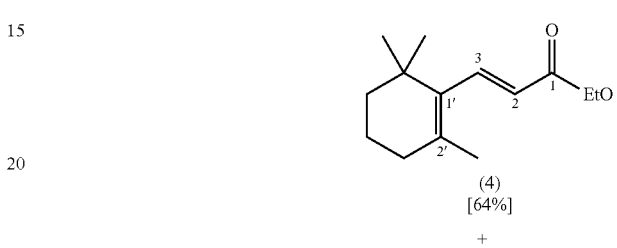

Scheme 1

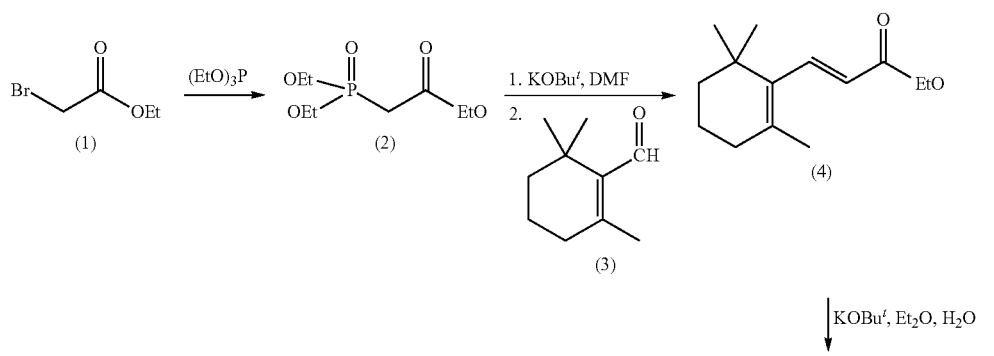

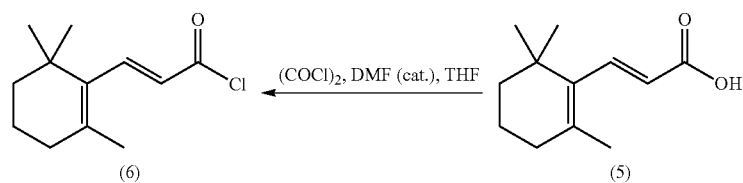

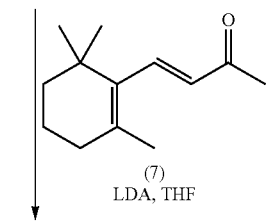

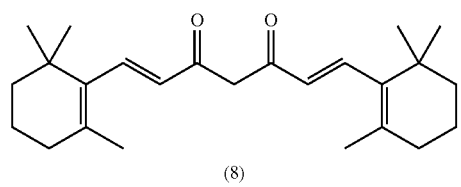

-continued

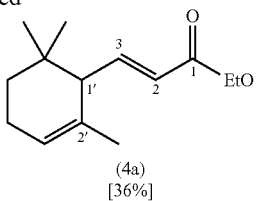

(4a) [36%]

Scheme 5

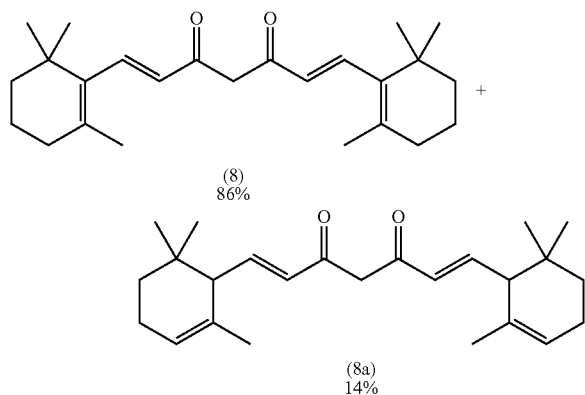

Scheme 5a

REFERENCES

1. Cuendet, M. and Pezzuto, J. M. (2000) The role of cyclooxygenase and lipoxygenase in cancer chemoprevention. Drug Metabol. Drug Interact., 17, 109-157.
2. Huang, M. T., Newmark, H. L. and Frenkel, K. (1997) Inhibitory effects of curcumin on tumorigenesis in mice. J. Cell Biochem. Suppl., 27, 26-34.
3. Conney, A. H., Lysz, T., Ferraro, T., Abidi, T. F., Manchand, P. S., Laskin, J. D. and Huang, M. T. (1991) Inhibitory effect of curcumin and some related dietary compounds on tumor promotion and arachidonic acid metabolism in mouse skin. Adv. Enzyme Regul., 31, 385-396.
4. Goel, A., Boland, C. R. and Chauhan, D. P. (2001) Specific inhibition of cyclooxygenase-2 (COX-2) expression by dietary curcumin in HT-29 human colon cancer cells. Cancer Lett., 172, 111-118.
5. Zhang, F., Altorki, N. K., Mestre, J. R., Subbaramaiah, K. and Dannenberg, A. J. (1999) Curcumin inhibits cyclooxygenase-2 transcription in bile acid- and phorbol ester-treated human gastrointestinal epithelial cells. Carcinogenesis, 20, 445-451.
6. Chun, K. S., Keum, Y. S., Han, S. S., Song, Y. S., Kim, S. H. and Surh, Y. J. (2003) Curcumin inhibits phorbol ester-induced expression of cyclooxygenase-2 in mouse skin through suppression of extracellular signal regulated kinase activity and NF-kB activation. Carcinogenesis, 24, 1515-1524.
7. Huang, M. T., Lysz, T., Ferraro, T., Abidi, T. F., Laskin, J. D. and Conney, A. H. (1991) Inhibitory effects of curcumin on in vitro lipoxygenase and cyclooxygenase activities in mouse epidermis. Cancer Res., 51, 813-819.
8. Rao, C. V., Rivenson, A., Simi, B. and Reddy, B. S. (1995) Chemoprevention of colon carcinogenesis by dietary curcumin, a naturally occurring plant phenolic compound. Cancer Res., 55, 259-266.
9. Jungil Hong, Mousumi Bose, Jihyeung Ju, Jae-Ha Ryu, Xiaoxin Chen, Shengmin Sang, Mao-Jung Lee and Chung S. Yang. (2004) Modulation of arachidonic acid metabolism by curcumin and related b-diketone derivatives: effects on cytosolic phospholipase A2, cyclooxygenases and 5-lipoxygenase. Carcinogenesis, 25, 1671-1679.
10. Liu Y, Chang R L, Cui X X, Newmark H L and Conney A H (1997) Synergistic effects of curcumin on all-trans retinoic acid- and 1 alpha,25-dihydroxyvitamin D3-induced differentiation in human promyelocytic leukemia HL-60 cells. Oncology Research, 9, 19-29.
11. Kawanishi S, Oikawa S and M Murata (2005) Evaluation for Safety of Antioxidant Chemopreventive Agents. Antioxidants & Redox Signaling, 7, 1728-1739.
12. Skrzypczak-Jankun Ewa, Zhou Kangjing, McCabe N. Patrick, Selman Steven and Jerzy Jankun. (2003) Structure of Curcumin in Complexes with Lipoxygenase and its Significance in Cancer. International Journal of Molecular Medicine., 12, 17-24.

All cited references are incorporated herein in their entirety.

What is claimed:

1. A compound of the following structures:

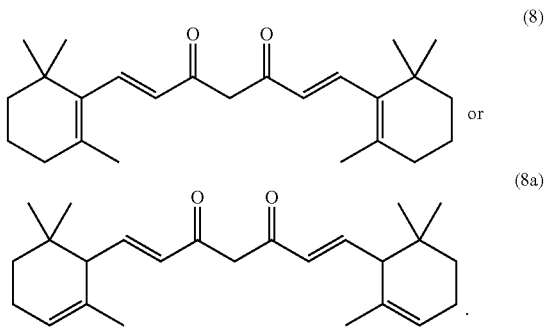

2. A compound of the following structures:

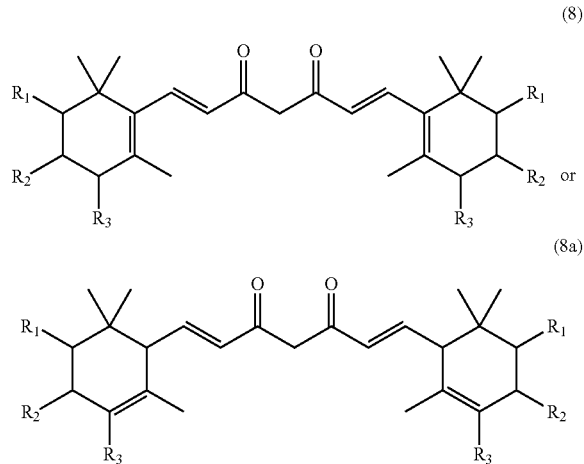

wherein R1, R2, and R3 are selected from the group consisting of H, OH, OCH3, and COOH.

3. A curcumin compound selected from the group consisting of the following structures:

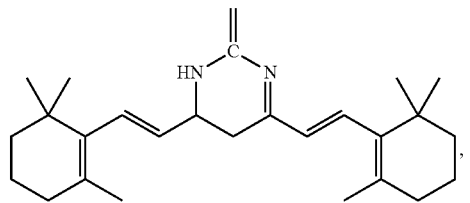
(13)

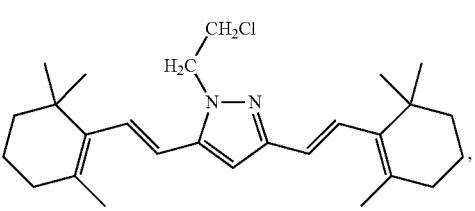
(14)

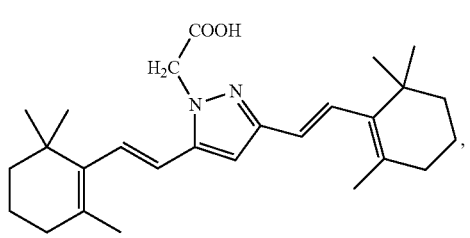
(15)

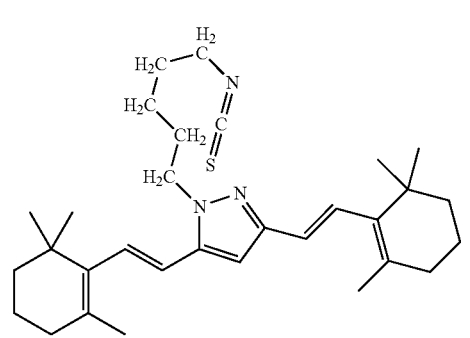
(16)

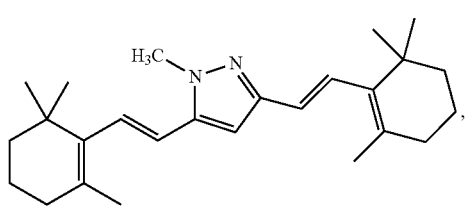
(17)

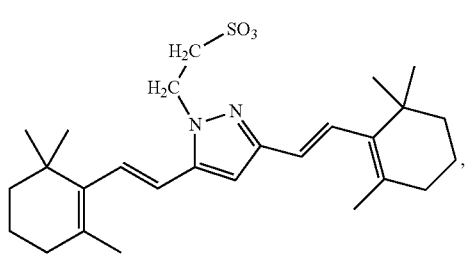
(18)

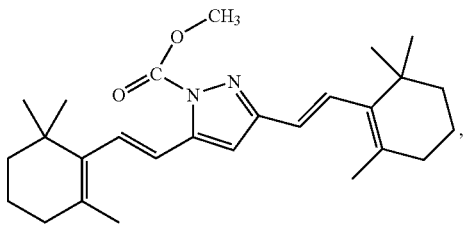
(19)

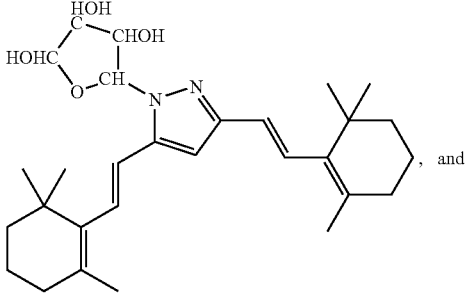
(20)

, and

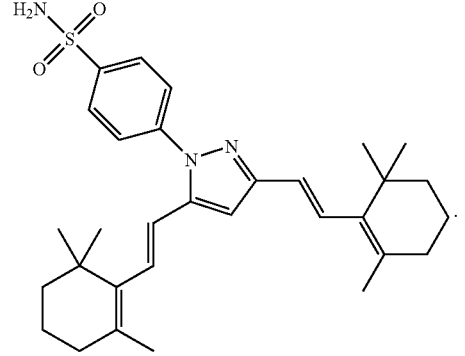
(21)

.

4. A curcumin compound having the following structure:

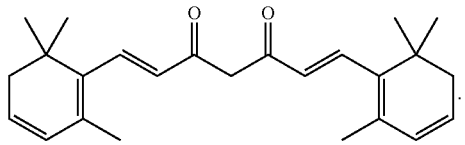
(8b)

.

5. A curcumin compound having the following structure:

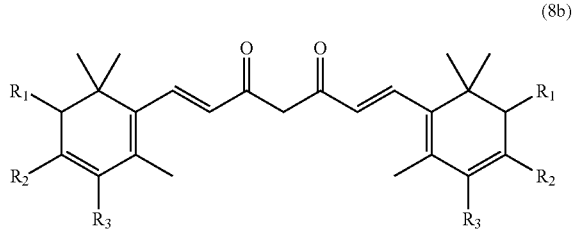
(8b)

wherein R1, R2, and R3 are selected from the group consisting of H, OH, OCH3, and COOH.

6. A method of therapeutically treating leukemia in a subject by administering a therapeutic amount of a compound of claim 1.

* * * * *